United States Patent [19]

Sarantakis

[11] 4,216,127
[45] Aug. 5, 1980

[54] ENKEPHALIN ANALOGUES

[75] Inventor: Dimitrios Sarantakis, West Chester, Pa.

[73] Assignee: American Home Products Corporation, New York, N.Y.

[21] Appl. No.: 54,549

[22] Filed: Jul. 5, 1979

[51] Int. Cl.$^2$ .................... C08L 37/00; C07C 103/52; A61K 37/00
[52] U.S. Cl. ................................ 260/8; 260/112.5 R; 424/177
[58] Field of Search ........................... 260/112.5 R, 8; 424/177

[56] References Cited

U.S. PATENT DOCUMENTS

| | | | |
|---|---|---|---|
| 4,075,190 | 2/1978 | Sarantakis | 260/112.5 R |
| 4,103,005 | 7/1978 | Li | 260/112.5 R |
| 4,143,032 | 3/1979 | Sarantakis | 260/112.5 R |
| 4,148,785 | 4/1979 | Dheer et al. | 260/112.5 R |
| 4,148,786 | 4/1979 | Sarantakis | 260/112.5 R |
| 4,162,307 | 7/1979 | Wilkinson | 260/112.5 R |

OTHER PUBLICATIONS

Frederickson et al., Opiates and Endogenous Opioid Peptides, (1976), 239–246.
Walker et al., Science, 196, (1977), 85–87.
Bayusz et al., Febs Letters, 76, No. 1, (1977), 91–92.

*Primary Examiner*—Delbert R. Phillips
*Attorney, Agent, or Firm*—Richard K. Jackson

[57] ABSTRACT

The polypeptides of the formula:

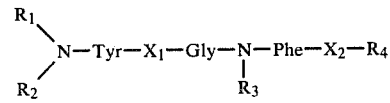

in which
$R_1$ is hydrogen, methyl, allyl, cyclopropylmethyl, cyclobutylmethyl or Arg;
$R_2$ is hydrogen or methyl;
$X_1$ is D-Asn or D-Gln;
$R_3$ is hydrogen or methyl;
$X_2$ is D-Asn, D-Gln or D-Cys; and
$R_4$ is the hydroxyl group of the 1-carboxy substituent of the C-terminal amino acid moiety or a lower alkyl ester, amide or lower alkyl amide thereof or the —$CH_2OH$ reduction product thereof;

or a pharmaceutically acceptable salt thereof; exert an analgesic effect in warm blooded animals.

7 Claims, No Drawings

ENKEPHALIN ANALOGUES

BACKGROUND OF THE INVENTION

The pentapeptides, Tyr—Gly—Gly—Phe—X[where X=Leu (I) or X=Met (II)] have been isolated and characterized by Hughes et al., Nature 258, 557 (1975). It was shown that they possess analgesic activity only after intracerebral (icv) administration, Belluzzi et al., Nature, 260 625 (1975). Pert et al., Science, 294, 330 (1976 reported that the pentapeptide Tyr—D—Ala—Gly—Phe—Met—NH$_2$ (III) exhibits potent and prolonged analgesia after icv administration. Bajusz et al., FEBS Leters 76, 91 (1977) by replacing Gly$^2$ with D—Met and the Met$^5$ by Pro—NH$_2$ obtained a very potent antinociceptive pentapeptide Tyr—D—Met—Gly—Phe—Pro—NH$_2$ (IV) which was 5.5 times more potent than morphine by intravenous administration. Romer et al., Nature, 268, 547 (1977) showed that the substituted tetrapeptide amide (V) possesses potent peripheral analgesic activity and some analgesic activity when given orally at high does (200–300 mg/kg.). Morgan et al., "Peptides, Proc. Fifth Amer. Pept.

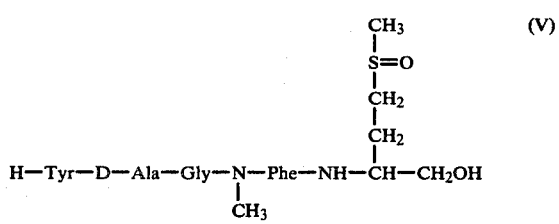

Symp." ed. Goodman and Meienhofer, p. 111 (1977) reported in vitro and in vivo biological activites of several enkephalin analogs among which was N(Me)-Tyr—Gly—Gly—Phe—Met—NH—Propyl (VI). Ling et al., ibid., p. 96 (1977) reported in vitro activities of several analogs of enkephaline with D-amino acids in position 5. Dutta et al., Life Sciences, 21, 559 (1977) and Dutta et al. Acta. Pharm. Sciences, 14, 14 (1977) described several analogs with D—Ser, D—Met, D—Ala, D—Thr, D—Lys (Boc), D—Phe, D—Leu, D—Asp and D—Ser(t-Bu) at position 2 and various substitutions with L-amino acids or amines at position 5. Belluzzi et al., Life Sciences, 23, 99 (1978) described analogs with D—Ala at position 2 and D—Leu or D—Met at position 5.

DESCRIPTION OF THE INVENTION

In accordance with this invention there is provided a group of analgesic agents of the formula:

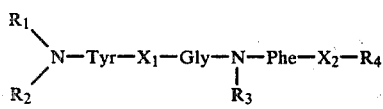

in which
R$_1$ is hydrogen, methyl, allyl, cyclopropylmethyl, cyclobutylmethyl or Arg;
R$_2$ is hydrogen or methyl;
X$_1$ is D—Asn or D—Gln;
R$_3$ is hydrogen or methyl;
X$_2$ is D—Asn, D—Gln or D—Cys; and
R$_4$ is the hydroxyl group of the 1-carboxy substituent of the C-terminal amino acid moiety or a lower alkyl ester, amide or lower alkyl amide thereof or the —CH$_2$OH reduction product thereof; or a pharmaceutically acceptable salt thereof.

In the preceding definition of the compounds of this invention, by the expression "lower alkyl" modifying the C-terminal esters and amides, applicant intends to embrace linear and branched chain alkyl groups of from one to six carbon atoms.

The pharmaceutically acceptable salts of the polypeptides of this invention are acid addition salts of the free base in which the acid may be either organic or inorganic, as for example, hydrochloric, phosphoric, maleic, acetic, citric, succinic, malic, and similar acids. Likewise, salts of the free peptidic acid are embraced by the expression "pharmaceutically acceptable salts", and include the sodium, potassium, ammonium, and lower alkylamine salts. The salts are prepared and isolated by conventional methods.

The analgesic polypeptides of this invention are prepared by typical, solid phase procedures employing either a benzhydrylamine polystyrene based resin for the production of the C-terminal amides, which is the preferred group representing R$^4$, or a chloromethylated or hydroxy methylated divinyl benzene crosslinked polystyrene resin for production of the C-terminal carboxylic acid or ester. The polypeptide is removed from the resin support with HF and purified by gel filtration. The C-terminal methylol group is produced by standard techniques.

The N-substituted tyrosine and phenylalanine derivatives employed in 1- and 4-positions of the polypeptide are prepared as reactants by reaction of methylchloride, allylchloride, cyclopropylmethyl chloride, etc. with a Boc protected ester of the approrpiate amino acid in the presence of silver oxide. The product is then saponified and hydrolyzed to obtain the desired reactant.

The following examples illustrate the preparation of the polypeptides of the invention.

EXAMPLE 1 tert-Butyloxycarbonyl-N-methyl-0,2,6-dichlorobenzyl-L-tyrosyl-D-asparaginyl-glycyl-N-methyl-L-phenylala-nyl-D-asparaginyl-benzhydrylamine polystyreme resin Benzhydrylamine polystyrene resin hydrochloride (Bachem. Inc.) (8 g.) containing approximately 0.4 mmoles/g. free amino groups, was placed in a reaction vessel of a peptide synthesizer Beckman 990A, and subjected to subsequent cycles of amino group deprotections and amino acid couplings as described in Program No. 1 and Program No. 2. The last program was performed in order to secure complete coupling of each amino acid. The following amino acids were incorporated onto the benzhydrylamine resin as described above, Boc—D—Asn—OH, Boc—N—Me—Phe—OH, Boc—Gly—OH, Boc—D—Asn—OH and Boc—N—Me—Tyr(Cl$_2$Bxl)OH, to afford the title peptiodoresin.

PROGRAM NO. 1

Peptide Synthesizer-Beckman 990

1. Wash with CH$_2$CL$_2 \times 3$.
2. Treat with TFA—CH$_2$Cl$_2$—EDT, 1:1:5% for 5 min.
3. Repeat (2) for 25 minutes.
4. Wash with CH$_2$Cl$_2 \times 4$.
5. Treat with TEA 12% in DMF for 1 minute.
6. Repeat (5) for 5 minutes.
7. Wash with CH$_2$Cl$_2 \times 3$.

8. Add 4 equivalents of Boc-protected amino acid and stir for 5 min.
9. Add 2 equivalents of 1M-DIC solution in DMF and stir for 25 min.
10. Add 2 equivalents of 1M-DIC solution in DMF and stir for 180 min.
11. Wash with $CH_2Cl_2 \times 3$.
12. Wash with methanol $\times 3$.

PROGRAM NO. 2

Peptide Synthesizer, Beckman 990

1. Wash with $CH_2Cl_2 \times 3$.
2. Add 2 equivalents of Boc-protected amino acid and stir for 5 min.
3. Add 2 equivalents of 1M-DIC solution in DMF and stir for 180 min.
4. Wash with DMF $\times 3$.
5. Wash with $CH_2Cl_2 \times 3$.
6. Wash with methanol $\times 3$.
7. Wash with $CH_2Cl_2 \times 3$.

EXAMPLE 2

N-Methyl-L-tyrosyl-D-asparaginyl-glycyl-N-methyl-L-phenylalanyl-D-asparaginyl amide acetate The peptidoresin of the previous example (11.5 g.) was mixed with anisole (25 ml.) and treated with liquid HF (150 ml.) at 0° C. for 60 minutes. The excess HF was evaporated under vacuo at 0° C. and the residue was extracted with 20% aqueous acetic acid, filtered and lyophilized to yield 4 g. of crude product. This crude material was chromatographed through a column of Sephadex G-10 (2.5×96 cm) and eluted with 10% aqueous acetic acid. The fractions (5.2 ml. each) in tubes 40 to 63 were pooled and lyophilized to yield 1.95 g. of semi-pure material. This material was chromatographed through a column of Sephadex G-25 (2.5×54 cm) equilibrated first with the lower phase of the biphasic system n-BuOH-water-acetic acid, 4-5-1, v/v, then with the upper phase. Elution with the upper phase provided the title compound in fractions (4 ml. each) 125 to 148 (221 mg.).

TLC, silica gel precoated glass plates Merck GOF-254

$R_f$(EtOAc-BuOH-water-AcOH, 1:1:1:1, v/v) 0.66
$R_f$(t-amyl alcohol-pyridine-water, 7:7:6, v/v) 0.70.

Amino acid analysis: Asp(2) 2.11, Gly, (1) 1, $NH_3$ (3) 3.14, N-Me-Tyr and N-Me-Phe N.D.

Similarly, by introduction of tert-butyloxycarbonyl-$N^g$-nitro-arginine as an additional last amino acid, the resulting product after deprotection is L-arginyl-L-tyrosyl-D-asparaginylglycyl-N-methyl-L-phenylalanyl-D-asparaginyl amide.

EXAMPLE 3

$N^\alpha$-tert-Butyloxycarbonyl-N-methyl-O-2,6-dichlorobenzyl-L-tyrosyl-D-glutaminyl-glycyl-N-methyl-L-phenylalanyl-D-glutaminyl benzhydrylamine polystyrene resin.

Benzhydrylamine polystyrene resin was treated in a fashion similar to Example 1 to afford the title peptidoresin.

EXAMPLE 4

$N^\alpha$-Methyl-L-tyrosyl-D-glutaminyl-glycyl-N-methyl-L-phenylalanyl-D-glutaminyl amide The peptidoresin of the previous example is treated with liquid HF under conditions similar to Example 2 to afford the crude title compound. This material is chromatographed through Sephadex G10 and eluted with 5% aq. AcOH to afford the title pentapeptide amide.

The analgesic activity of the polypeptides of this invention was demonstrated following a modification of the phenylbenzoaquinone induced writhing test procedure of Seigmund et al., Proc. Soc. exp. Biol. Med. 95 729–731 (1957), in which groups of ten CF-1 mice were administered, subcutaneously, known dosages of N(Me)Tyr—D—Asn—Gly—N(Me)Phe—D—Asn—$NH_2$, as a compound representative of the group of compounds of this invention. Five minutes later, each animal received, i.p., 0.25 ml. of a 0.02 percent phenylbenzoquinone solution. The animals were observed over a ten minute period following the phenylbenzoquinone injection for the presence of writhing. Animals not writhing were considered to exhibit analgesia. The dose-response analysis was then performed according to Litchfiled et al., J. Pharmacol. exp. Therap. 96 99—113(1949). The $ED_{50}$ for the test compound was 1.0 mg/kg (0.62–1.6) at 30 minutes by subcutaneous administration. Following the same procedure, analgesia was observed at a dose of 10 mg/kg for a period of forty five minutes in 100 percent of the animals.

The test results demonstrate that the compounds of this invention induce analgesia upon administration of a single subcutaneous injection at a dose as low as 10 milligrams per kilogram. For practical purposes, it is contemplated, based upon the proceding test results, that a unit does of from about 0.1 to about 20 milligrams per kilogram for single or plural administrations is the appropriate dosage to achieve that degree of analgesia desired for various applications. The exact dose to be employed will, of course, vary with the specific compound employed, the patient and the degree of analgesia desired. The determination of a precise dose for production of a desired effect is readily determined empirically by the physician. The route of administration, whether subcutaneous, intravenous, intramuscular or oral, etc., must also be considered by the physician using the compounds disclosed therein because the degree of response is obviously related to the route of administration.

The protected intermediates for the linear and cyclic polypeptides disclosed herein form an additional aspect of the invention. The intermediates are of the formula:

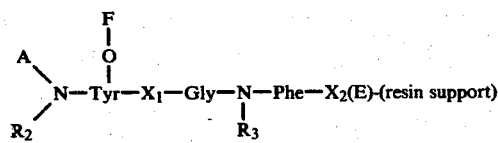

in which
R$^2$, R$^3$, X$_1$ and X$_2$ are defined supra,
A is hydrogen or an α-amino protecting group or alpha amino protected N-guanyl protected arginyl;
R is a protecting group for the phenolic hydroxy group of tyrosyl; and
E is a protecting group for the mercapto group of the C-terminal D-Cys moiety when present.

Of the many protecting groups known to the art for use in conjunction with each of the functional groups found in the depicted polypeptide intermediate, the most preferred are tert-butyloxycarbonyl (Boc) for the α-amino group of the arginyl or tyrosyl moiety, nitro ($NO_2$) for the guanyl group of the arginyl moiety, 2,6-dichlorobenzyl (Cl₂Bzl) for the phenolic hydroxyl group of the tyrosyl moiety, p-methoxybenzyl (MBzl) for the mercapto group of the C-terminal D-cysteinyl moiety. Because the C-terminal amides are the preferred final product, the resin support in the intermediates is preferably a benzhydrylamine polystyrene resin.

What is claimed is:

1. A compound of the formula:

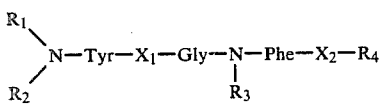

in which
R₁ is hydrogen, methyl, allyl, cyclopropylmethyl, cyclobutylmethyl or Arg;
R₂ is hydrogen or methyl;
X₁ is D—Asn or D—Gln;
R₃ is hydrogen or methyl;
X₂ is D—Asn, D—Gln or D—Cys; and
R₄ is the hydroxyl group of the 1-carboxy substituent of the C-terminal amino acid moiety or a lower alkyl ester, amide or lower alkyl amide thereof or the —CH₂OH reduction product thereof; a protected peptido resin thereof;
or a pharmaceutically acceptable salt thereof.

2. The compound of claim 1 which is N-methyl-L-tyrosyl-D-asparaginyl-glycyl-N-methyl-L-phenylalanyl-D-asparaginyl amide or a pharmaceutically acceptable salt thereof.

3. The compound of claim 1 which is N-methyl-L-tyrosyl-D-glutaminyl-glycyl-N-methyl-L-phenylalanyl-D-glutaminyl amide or a pharmaceutically acceptable salt thereof.

4. A protected peptidoresin of claim 1 of the formula:

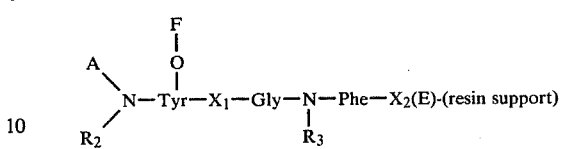

in which
A is hydrogen, an α-amino protecting group or α-amino protected, N-guanyl protected arginyl;
R₂ is hydrogen or methyl;
F is a phenolic hydroxy protecting group;
X₁ is D—Asn or D—Gln;
R₃ is hydrogen or methyl;
X₂ is D—Asn, D—Gln or D—Cys wherein E is a mercapto protecting group for D—Cys.

5. The compound of claim 4 in which A is tert-butyloxycarbonyl-(Nᵍ—NO₂)Arg, F is 2,6-dichlorobenzyl, R₂ is hydrogen, X₁ is D—Asn, R₃ is methyl, X₂ is D—Asn and the resin support is benzhydrylamine polystyrene resin.

6. The compound of claim 4 in which A is tert-butyloxycarbonyl, R₂ is methyl, F is 2,6-dichlorobenzyl, X₁ is D—Asn, R₃ is methyl, X₂ is D—Asn and the resin support is benzhydrylamine polystyrene resin.

7. The compound of claim 4 in which A is tert-butyloxycarbonyl, R₂ is methyl, F is 2,6-dichlorobenzyl, X₁ is D—Gln, R₃ is methyl, X₂ is D—Gln and the resin support is benzhydrylamine polystyrene resin.

* * * * *